United States Patent [19]

Gates

[11] Patent Number: 4,795,483
[45] Date of Patent: Jan. 3, 1989

[54] HERBICIDES
[75] Inventor: Peter S. Gates, Cambridge, England
[73] Assignee: Schering Agrochemicals, England
[21] Appl. No.: 43,370
[22] Filed: Apr. 28, 1987
[30] Foreign Application Priority Data
Apr. 30, 1986 [GB] United Kingdom ............... 8610530
[51] Int. Cl.$^4$ ................. C07D 513/04; A01N 43/90
[52] U.S. Cl. ................................. 71/90; 546/271; 548/149; 548/154
[58] Field of Search ............... 548/154, 149; 71/90; 546/271

[56] References Cited

U.S. PATENT DOCUMENTS 3,957,977  5/1976  Hoffmann ............... 548/154
4,415,690 11/1983  Grimm ................... 524/117

FOREIGN PATENT DOCUMENTS 26514    7/1911  Japan .................... 518/154
1560988  2/1980  United Kingdom .
1571481  7/1980  United Kingdom .

OTHER PUBLICATIONS

March, Advanced Organic Chemistry, p. 445, (1985).

Primary Examiner—Robert Gerstl
Attorney, Agent, or Firm—Ostrolenk, Faber, Gerb & Soffen

[57] ABSTRACT

The invention provides certain herbicidal thiazolo-triazole sulphonamides, processes for their preparation, and compositions containing them, the compounds being of the formula:

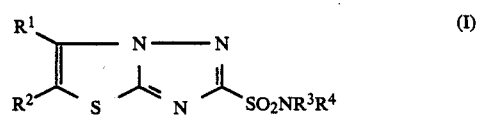

(I)

where:

$R^1$ and $R^2$, which may be the same or different, each represent hydrogen, hydroxy, halo, cyano, substituted or unsubstituted alkyl, alkoxy, alkenyloxy, alkynyloxy, aryl, aralkyl, heteroaryl or carbamoyl, or a group —$COR^a$ or —$CO_2R^a$ or where $R^a$ is hydrogen or alkyl; or $R^1$ and $R^2$ together represent an alkylene chain of 3 or 4 carbon atoms;

$R^3$ represents a substituted or unsubstituted aryl, heterocyclyl or benzheterocyclyl group; and $R^4$ represents hydrogen, an alkali-metal atom, an ammonium group, a substituted or unsubstituted alkyl, alkenyl, alkynyl, acyl, alkoxycarbonyl or aralkyl group, a heterocyclic group, or a group of the formula:

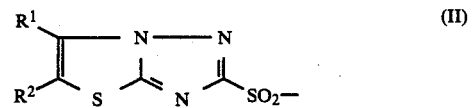

(II)

where $R^1$ and $R^2$ are as defined hereinbefore.

19 Claims, No Drawings

HERBICIDES

This invention concerns herbicidal thiazolotriazole sulphonamides, processes for their preparation, and compositions containing them.

In one aspect, the invention provides the thiazolotriazole sulphonamides of the formula:

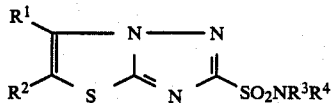
(I)

where:

$R^1$ and $R^2$, which may be the same or different, each represent hydrogen, hydroxy, halo, cyano, substituted or unsubstituted alkyl, alkoxy, alkenyloxy, alkynyloxy, aryl, aralkyl, heteroaryl or carbamoyl, or a group —$COR^a$ or —$CO_2R^a$ or where $R^a$ is hydrogen or alkyl; or $R^1$ and $R^2$ together represent an alkylene chain of 3 or 4 carbon atoms;

$R^3$ represents a substituted or unsubstituted aryl, heterocyclyl or benzheterocyclyl group; and $R^4$ represents hydrogen, an alkali-metal atom, an ammonium group, a substituted or unsubstituted alkyl, alkenyl, alkynyl, acyl, alkoxycarbonyl or aralkyl group, a heterocyclic group, or a group of the formula:

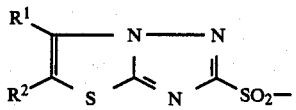
(II)

where $R^1$ and $R^2$ are as defined hereinbefore.

When $R^1$ or $R^2$ represents halo, it is preferably chloro or bromo.

When any of $R^1$, $R^2$ and $R^4$ is or contains an alkyl group, that group is preferably of 1 to 6 carbon atoms, especially of 1 to 4 carbon atoms, for example methyl, ethyl, n-propyl, isopropyl, n-butyl or t-butyl. The group may be unsubstituted, or substituted for example by one or more halogen atoms, carboxy groups, cyano groups or alkoxycarbonyl groups of 1 to 4 carbon atoms, specific preferred substituted groups being chloromethyl, fluoromethyl, cyanomethyl, carboxymethyl, trifluoromethyl, methoxycarbonylmethyl and ethoxycarbonylmethyl.

When $R^1$ or $R^2$ represents alkenyloxy or alkynyloxy, it is preferably of 2 to 6 carbon atoms, for example allyloxy or propargyloxy.

When $R^1$ or $R^2$ represents a group —$COR^a$ or —$CO_2R^a$, $R^a$ is preferably hydrogen or alkyl of 1 to 4 carbon atoms, particularly methyl or ethyl, specific preferred such groups being formyl, acetyl, carboxy, methoxycarbonyl and ethoxycarbonyl.

When $R^1$ or $R^2$ represents an aryl or aralkyl group, it is preferably phenyl or benzyl, which may be unsubstituted, or substituted for example by one or more halogen atoms, nitro groups, cyano groups, or alkyl or alkoxy groups of 1 to 4 carbon atoms.

When $R^1$ or $R^2$ represents a heteroaryl group, that group is preferably a nitrogen-containing heterocycle, particularly a 5- or 6-membered single ring heterocycle, eg pyrrolyl, pyridyl, furyl, 2-thienyl, pyrimidinyl, 1-triazolyl or 1-imidazolyl.

$R^1$ and $R^2$ independently preferably represent hydrogen or an unsubstituted alkyl group of 1 to 6 carbon atoms, eg methyl. It is particularly preferred that one of $R^1$ and $R^2$ is hydrogen, and the other is hydrogen or methyl.

When $R^3$ represents an aryl group, it is preferably a phenyl group, which is desirably substituted by one or more alkyl, alkoxy, alkoxycarbonyl or alkylthio groups of 1 to 4 carbon atoms (which may themselves be further substituted), halogen atoms, cyano groups, aminosulphonyl groups or nitro groups, especially a phenyl group substituted by one or more chlorine, bromine or fluorine atoms, and/or one or more methyl, methoxy, trifluoromethyl, methylthio, methoxycarbonyl, ethoxycarbonyl or nitro groups.

When $R^3$ represents heterocyclyl, it is preferably a 5- or 6-membered group which contains nitrogen, oxygen and/or sulphur. Specific preferred heterocyclic groups include pyridyl, 2-thienyl, pyrimidinyl, thiazolyl, 1,2,4-thiadiazolyl, triazolyl and triazinyl.

When $R^3$ represents a benzheterocyclyl group, it is preferably a benzthiophene, benzodioxole, quinoline, quinazoline, benzothiazole or dihydrobenzofuran group.

When $R^4$ represents an alkali-metal, it is preferably sodium or potassium.

When $R^4$ represents an ammonium group, that group may, if desired, be substituted, eg by one or more alkyl groups of 1 to 4 carbon atoms.

When $R^4$ represents an alkenyl or alkynyl group, it is preferably of 2 to 6 carbon atoms, for example vinyl, allyl or propargyl.

When $R^4$ represents acyl or alkoxycarbonyl, it is preferably of 2 to 6 carbon atoms, eg acetyl, propanoyl, methoxycarbonyl or ethoxycarbonyl.

When $R^4$ represents aralkyl, it is preferably benzyl, which may, if desired, be substituted by one or more halogen atoms (especially chlorine or bromine), alkyl or alkoxy groups of 1 to 4 carbon atoms, eg methyl, ethyl, methoxy or ethoxy, nitro groups or cyano groups.

When $R^4$ represents a heterocyclyl group, it is preferably a nitrogen-containing heterocycle, particularly a 5- or 6-membered single ring heterocycle, eg pyridyl or pyrimidinyl.

$R^4$ preferably represents hydrogen.

In a particularly preferred group of compounds of formula I, $R^1$ and $R^2$ each represent hydrogen or methyl, $R^3$ is a phenyl group substituted by one or more alkyl, alkoxy, alkoxycarbonyl or alkylthio groups of 1 to 4 carbon atoms, cyano groups, aminosulphonyl groups, halogen atoms or nitro groups, and $R^4$ is hydrogen. Especially preferred substituents on the phenyl group which $R^3$ represents are methyl, ethyl, methoxy, ethoxy, methylthio, methoxycarbonyl, ethoxycarbonyl, cyano and nitro.

Particularly preferred compounds according to the invention are those of the Examples provided hereinafter. Specific mention may be made, however, of N-(2,6-difluorophenyl)thiazolo[3,2-b][1,2,4]triazole-2-sulphonamide.

In another aspect, the invention provides a process for the preparation of a thiazolotriazole sulphonamide of formula I, in which a thiazolotriazole sulphonyl halide of the formula:

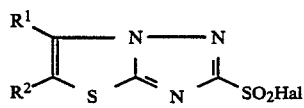

where $R^1$ and $R^2$ are as defined hereinbefore, and Hal represents halogen, is reacted in the presence of a base with an amine of the formula $R^3R^4NH$ where $R^3$ and $R^4$ are as defined hereinbefore to give the desired compound.

The reaction is conveniently effected at a temperature of from $-10°$ C. to $100°$ C., particularly from $-10°$ C. to $25°$ C., conveniently at room temperature.

The base is preferably an organic base, especially a tertiary organic base, for example pyridine, N,N-dimethylaniline or triethylamine, or an excess of the amine $R^3R^4NH$. The reaction may be catalysed by certain tertiary organic bases, for example dimethylaminopyridine.

The product of the reaction in which $R^4$ represents hydrogen is able to react with any excess sulphonyl halide of formula III present to give the compounds of formula I where $R^4$ represents a group of formula II. Consequently, the molar amounts of sulphonyl halide and amine employed should be chosen appropriately to give the desired compound. To prevent the formation of bis-compounds, the amine is preferably employed in a 1 to 5 times molar excess.

The compounds of formula III may themselves be prepared by reacting a compound of the formula:

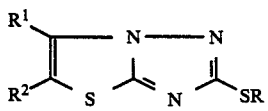

where $R^1$ and $R^2$ are as defined hereinbefore, and R represents hydrogen, aralkyl or acyl, with the appropriate halogen or, in the presence of wet silica gel, with the appropriate sulphuryl halide, to give the desired compound.

The reaction is desirably effected with cooling to less than ambient temperature, eg to a temperature of from $-10°$ C. to $5°$ C.

Where a halogen is used, it is conveniently passed into a solution or suspension of the appropriate starting material in an aqueous medium, eg aqueous acetic acid or hydrochloric acid.

Where a sulphuryl halide is employed, the reaction is preferably effected in a suitable solvent medium, eg dichloromethane.

In turn, the compounds of formula IV may be prepared by reacting the corresponding mercaptotriazole of the formula:

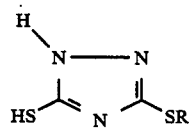

where R is as defined hereinbefore, in a suitable solvent medium, with a compound of the formula:

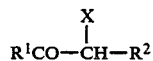

where $R^1$ and $R^2$ are as defined hereinbefore and X represents halogen, or with an acetal of such a compound where $R^1$ represents hydrogen in the presence of a base and followed by hydrolysis, to give the desired compound.

The solvent medium employed is preferably an alkanol such as ethanol, and the reaction is desirably carried out with heating, eg to reflux.

The compounds of formula V where R is other than hydrogen may be prepared from the corresponding compounds where R is hydrogen by reaction thereof in the presence of a base with the appropriate halide RHal where R is as defined hereinbefore and Hal represents halogen.

The compounds of formula I may be interconverted, if desired, into other compounds of formula I by methods known per se. For example, the compounds of formula I in which $R^4$ represents hydrogen may be acylated by means of the appropriate acid anhydride or chloride to give the corresponding compounds in which $R^4$ represents acyl, or may be reacted with a suitable alkyl chloroformate to give compounds where $R^4$ is alkoxycarbonyl. Carboxyl groups present may be esterified by known methods. Ester groups present may be hydrolysed to carboxyl groups, and acyl groups may be removed by hydrolysis. Alternatively, compounds of formula I which contain a carboxyl group may be converted by known amidation techniques into the corresponding amides, and thence, if desired, to the corresponding cyano compounds. Salts of the compounds of formula I, ie those in which $R^4$ represents an alkalimetal or ammonium group, may be prepared from the corresponding compounds in which $R^4$ is hydrogen by reaction with the appropriate base, eg an alkali-metal t-butoxide, or the appropriate amine. The salts may of course be hydrolysed to the corresponding compounds in which $R^4$ is hydrogen. The compounds of formula I in which $R^4$ represents a group of formula II may also be hydrolysed to the corresponding compounds in which $R^4$ is hydrogen.

Such techniques, and the conditions to be employed, are well-known to those skilled in the art, and experimental details of typical conversions are provided hereinafter.

The compounds of formula I are herbicidally-active against a wide range of broad-leaved and grassy weeds, but are comparatively safe to certain crop species. They may thus be of use as selective herbicides, particularly in the control of a range of weeds in cereals or other crops, eg wheat, barley, maize, soya beans, oilseed rape, cotton, sugar beet, rice or sunflowers.

In another aspect, the invention provides a herbicidal compositions which comprises one or more compounds of formula I in association with a suitable carrier and/or surface active agent.

The compositions usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise nonionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The present active compounds, especially those of the Examples provided hereinafter, and particularly N-(2,6-difluoro-phenyl)thiazole[3,2-b][1,2,4]triazole-2-sulphonamide, may be admixed with another pesticide, eg a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, and especially isoproturon, methabenzthiazuron, trifluralin, ioxynil, bromoxynil, benazolin, mecoprop, fluroxypyr, alachlor, acifluorfen, lactofen, metribuzin and pendimethalin.

The present compounds may be applied to plants, the soil, land or aquatic areas, and particularly to a locus at which a crop is growing or is about to grow. The compounds are active both pre- and post-emergence.

The invention is illustrated by the following Examples, in which Me=methyl, Et=ethyl, Pr=propyl, Bu=butyl, Py=pyridyl and Ph=phenyl.

EXAMPLE 1

N-(2-chloro-6-methylphenyl)-6-methylthiazolo[3,2-b][1,2,4]triazole-2-sulphonamide (a) 3-Benzylthio-5-mercapto-1,2,4-triazole Sodium methoxide (35.1 g) was added portionwise to 3,5-dimercapto-1,2,4-triazole (86.4 g) in methanol (400 ml) with stirring and cooling to 5° to 15° C. under nitrogen. After stirring for 5 minutes, the formed derivative was treated dropwise with benzyl chloride (79.7 g) at 5° to 10° C. over a period of 1 hour. The mixture was then stirred for about 20 hours at ambient temperature, then filtered. The precipitate was washed with a little ice-cold methanol, and then with water, to give 83.2 g of desired product, mp 199°–201° C.

(b) 2-Benzylthio-6-methylthiazolo[3,2-b][1,2,4]triazole

The product of stage (a) (22.3 g) and chloroacetone (9.6 g) were heated in ethanol (120 ml) under reflux for 22 hours. The solution was then reduced under vacuum, and the residue was stirred with a mixture of ether and aqueous sodium bicarbonate. The ether solution was separated, washed with water, dried over magnesium sulphate, and reduced under vacuum to give 24.1 g of the desired product as an orange oil.

(c) 6-Methylthiazolo[3,2-b][1,2,4]triazole-2-sulphonyl chloride

Chlorine gas was bubbled slowly through a stirred mixture of the product of stage (b) (13 g) in acetic acid (50 ml) and water (50 ml) at less than 5° C. over about ½ hour. The mixture was stirred for 15 minutes, then filtered, and the precipitate was washed wth water followed by petroleum ether (bp 40°–60° C.) to give, after drying over calcium chloride, 7.9 g of desired product, mp 125°–129° C. Washing with ether gave pure product, mp 133°–134° C.

(d) N-(2-chloro-6-methylphenyl)-6-methyl-thiazolo[3,2-b][1,2,4]triazole-2-sulphonamide The product stage (c) (2.0 g) was added portionwise to 2-chloro-6-methylaniline (1.3 g) in pyridine (8 ml) with stirring and cooling to 5° to 10° C. After standing for 4 days at room temperature, the mixture was treated with ether and dilute hydrochloric acid. The precipitate was filtered off and washed with dilute hydrochloric acid, water, and then ether to give 1.9 g of crude product. Recrystallization from ethanol gave 1.0 g of pure product, mp 201°-203° C.

EXAMPLE 2

N-(2-chlorophenyl)-6-methylthiazolo[3,2-b][1,2,4]triazole-2-sulphonamide (a) 6-Methylthiazolo[3,2-b][1,2,4]triazole-2-sulphonyl chloride—Alternative route Sulphuryl chloride (9.7 g) in dichloromethane (5 ml) was added dropwise to a stirred mixture of the product of Example 1, stage (b) (5.0 g) in dichloromethane (40 ml) containing wet silica gel (12 g silica gel 60–120 mesh plus 1.2 ml water) at 5°-10° C. The mixture was stirred at about 5° C. for 2 hours, then filtered, and the filtrate was run down under vacuum. The residue was triturated with petroleum ether (bp 40°-60° C.) to yield 2.8 g of crude product, mp 115°-125° C.

(b) N-(2-chlorophenyl)-6-methylthiazolo[3,2-b][1,2,4]triazole-2-sulphonamide

The product of stage (a) (3.0 g) was added portionwise with stirring and cooling to 5°-10° C. to 2-chloroaniline (10 g). The mixture was stirred for 20 hours at ambient temperature. Ether and water were added and, after 5 minutes stirring, the precipitated solid was filtered off and washed with water and ether. The yield of product was 3.4 g, mp 172°-174° C.

EXAMPLE 3

N-(2-chloro-6-methylphenyl)-thiazolo[3,2-b][1,2,4]triazole-2-sulphonamide (a) 3-benzylthio-5-(2,2-dimethoxyethylthio)-1,2,4-triazole Bromoacetaldehyde dimethyl acetal (7.8 g) was added portionwise to 3-benzylthio-5-mercapto-1,2,4-triazole (10 g) and sodium methoxide (2.5 g) in dimethylformamide (60 ml) under nitrogen. The mixture was heated at about 110° C. for 5 hours. Addition to water and isolation through ether gave 12.6 g of desired product, mp 73°-76° C.

(b) 2-Benzylthio-5,6-dihydro-6-hydroxythiazolo[3,2-b][1,2,4]triazole

The product of stage (a) was heated under reflux with dilute hydrochloric acid (15 ml conc. plus 100 ml water) for 3 hours. The mixture was then cooled and stirred with ether. The precipitated solid was filtered off to give 5.4 g of desired product, mp 136°-138° C.

(c) 2-Benzylthiothiazolo[3,2-b][1,2,4]triazole

The product from stage (b) (7.9 g) was dissolved in dichloromethane (50 ml) and was treated with pyridine (2.7 g), then with thionyl chloride (4.2 g) in dichloromethane (5 ml) dropwise with stirring at 5°-10° C. After 3 hours stirring at room temperature, the solution was washed with water, dilute hydrochloric acid, aqueous sodium bicarbonate solution and water again, dried and run down to give the desired product as a brown oil which was recrystallise from ethanol to give pure product, mp 91°-93° C.

(d) N-(2-chloro-6-methylphenyl)thiazolo[3,2-b][1,2,4]triazole-2-sulphonamide

By methods analogous to those of Examples 1c and 2b, the above compound was prepared in a yield of 50%, mp 218°-220° C.

EXAMPLES 4–118

The following compounds of formula I where $R^4$ represents hydrogen were prepared by methods analogous to those of the stages of Examples 1, 2 and/or 3 stated:

| No | R1 | R2 | R3 (Ph subst:) | M Pt (°C.) | Stages |
| --- | --- | --- | --- | --- | --- |
| 4 | Me | H | 2,6-diCl | 261–263 | 1c/1d |
| 5 | Me | H | 2,6-diCl,3-Me | 252–254 | 1c/1d |
| 6 | Me | H | 2-CF₃ | 197–199 | 1c/2b |
| 7 | Me | H | 2,6-diMe | 199–201 | 1c/2b |
| 8 | Me | H | 2,6-diF | 175–177 | 1c/2d |
| 9 | Me | H | 2-iPr | 175–177 | 1c/2b |
| 10 |  | —(CH₂)₄— | 2-Cl | 199–200 | 2a/2b |
| 11 |  | —(CH₂)₄— | 2-Cl,6-Me | 250–252 | 2a/2b |
| 12 | Ph | Cl | 2-Cl,6-Me | 219–220 | 1c/2b |
| 13 | Me | Me | 2-Cl,6-Me | 235–237 | 2a/2b |
| 14 | Ph | Cl | 2,6-diCl,3-Me | 197–199 | 1c/1d |
| 15 | Me | H | 2,6-diBr | 251–260 | 1c/1d |
| 16 | Me | H | 2-Me,3-NO₂ | 245–247 | 1c/1d |
| 17 | Me | Me | 2,6-diCl | 240–242 | 2a/1d |
| 18 | t-Bu | H | 2-Cl,6-Me | 199–201 | 2a/2b |
| 19 | Me | H | 2,3-diMe,6-NO₂ | 247–249 | 1c/1d |
| 20 | Me | H | Ph | 195–197 | 1c/2b |
| 21 | Et | H | 2-Cl,6-Me | 231–233 | 2a/2b |
| 22 | Me | H | 2-Me,3-Cl | 197–199 | 1c/2b |
| 23 | H | Me | 2,6-diCl | 248–252 | 3/2a/1d |
| 24 | H | Me | 2,6-diCl,3-Me | 232–236 | 3/2a/1d |
| 25 | t-Bu | H | 2,6-diCl | 225–226 | 2a/1d |
| 26 | Et | H | 2,6-diCl | 292 | 2a/1d |
| 27 | Me | H | 2,3-diCl | 181–183 | 1c/1d |
| 28 | Me | H | 2,6-diEt | 186–188 | 1c/2b |
| 29 | Me | Me | 2-CF₃ | 174–175 | 2a/2b |
| 30 | Me | H | 2-F | 178–179 | 1c/2b |
| 31 | Me | H | 2-I | 175–177 | 1c/1d |

-continued

| No | R1 | R2 | R3 (Ph subst:) | M Pt (°C.) | Stages |
|---|---|---|---|---|---|
| 32 | Me | Me | 2,6-diF | 205–207 | 2a/1d |
| 33 | Me | Me | 2,6-diCl,3-Me | 225–227 | 2a/1d |
| 34 | H | Me | 2-Cl,6-MeS | 229–230 | 3/2a/1d |
| 35 | Me | H | 2-Cl,6-F | 237–239 | 1c/1d |
| 36 | H | Me | 2-Cl,6-F | 227–230 | 3/2a/1d |
| 37 | Me | Me | 2-Cl,6-F | 216–218 | 2a/1d |
| 38 | Ph | Me | 2-Cl,6-F | 240–243 | 2a/1d |
| 39 | Me | H | 2-Me,6-$NO_2$ | 237–241 | 1c/1d |
| 40 | Me | H | 2-Cl,6-MeS | 266–270 | 1c/1d |
| 41 | Ph | Me | 2,6-diF | 200–201 | 2a/1d |
| 42 | Ph | Me | 2-Cl,6-Me | 218–220 | 2a/2b |
| 43 | Me | H | 2,3,5,6-tetraF | 252–254 | 1c/1d |
| 44 | Me | Me | 2-Cl,6-MeS | 237–240 | 2a/1d |
| 45 | Ph | Me | 2-Cl,6-MeS | 279–280 | 2a/1d |
| 46 | Ph | H | 2,6-diF | 263–269 | 2a/1d |
| 47 | Ph | H | 2,6-diCl | 218–223 | 2a/1d |
| 48 | Ph | H | 2-Cl,6-Me | 198–202 | 2a/2b |
| 49 | Ph | H | 2,6-diCl,3-Me | 221–225 | 2a/1d |
| 50 | 4-ClPh | H | 2,6-diF | 238–242 | 2a/1d |
| 51 | Me | COOMe | 2,6-diF | 229–233 | 2a/1d |
| 52 | 4-Cl | H | 2-Cl,6-Me | 242–245 | 2a/2b |
| 53 | Ph | H | 2-Cl,6-MeS | 248–250 | 2a/1d |
| 54 | Ph | H | 2-Me,6-$NO_2$ | 235–238 | 2a/1d |
| 55 | Me | COOMe | 2-Cl,6-MeS | 191–194 | 2a/1d |
| 56 | Me | COOMe | 2-Cl,6-Me | 197–199 | 2a/2b |
| 57 | 2-Py | H | 2-Cl,6-Me | 231–233 | 2a/2b |
| 58 | Me | H | 2-COOEt,6-Me | 128–129 | 1c/1d |
| 59 | H | H | 2-Cl,6-MeS | 290–293 | 3/2a/1d |
| 60 | Me | COOEt | 2,6-diF | 188–190 | 2a/1d |
| 61 | Me | COOEt | 2-Cl,6-Me | 163–165 | 2a/2b |
| 62 | Me | H | 2-COOMe,6-Me | 151–152 | 1c/1d |
| 63 | $ClCH_2$ | H | 2-Cl,6-Me | 233–235 | 2a/2b |
| 64 | 2-Py | H | 2,6-diF | 269–273 | 1c/1d |
| 65 | $ClCH_2$ | H | 2,6-diF | 210–215 | 2a/1d |
| 66 | Me | COMe | 2-Cl,6-Me | 245–248 | 1c/2b |
| 67 | 2-Py | H | 2-Cl,6-MeS | 290–300 | 1c/1d |
| 68 | 2-Py | H | 2,6-diCl,3-Me | 236–237 | 1c/1d |
| 69 | Me | COMe | 2,6-diCl | 252–256 | 1c/1d |
| 70 | Me | COMe | 2,6-diF | 228–231 | 1c/1d |
| 71 | H | H | 2,6-diF | 222–223 | 3/1c/1d |
| 72 | Me | COOEt | 2,6-diCl,3-Me | 155–160 | 2a/1d |
| 73 | H | H | 2-COOMe,6-Me | 128–130 | 3/1c/1d |
| 74 | $EtOOCCH_2$ | H | 2,6-diF | 154–156 | 1c/1d |
| 75 | $EtOOCCH_2$ | H | 2-Cl,6-Me | 144–145 | 1c/2b |
| 76 | H | Me | 2-COOMe,6-Me | 165–169 | 3/2a/1d |
| 77 | Me | Me | 2-COOMe,6-Me | 169–171 | 2a/1d |
| 78 | Me | H | 2-Cl,6-EtS | 238–243 | 1c/1d |
| 79 | Me | H | 2-Cl,6-iPrS | 200–210 | 1c/1d |
| 80 | Me | H | 2-COOMe | 170–172 | 1c/2b |
| 81 | Me | H | 2,5-diF | 167–168 | 1c/1d |
| 82 | Me | H | 3-Cl,2-MeO | 166–168 | 1c/1d |
| 83 | Me | H | 2,4,6-triF | 250–252 | 1c/1d |
| 84 | Me | COMe | 2,6-diCl,3-Me | 232–236 | 1c/1d |
| 85 | $EtOOCCH_2$ | H | 2,6-diCl,3-Me | 160–163 | 1c/1d |
| 86 | Me | H | 2-Br,6-MeO | 261–264 | 1c/1d |
| 87 | Me | Me | 2-Br,6-MeO | 207–209 | 2a/1d |
| 88 | Me | Me | 2-COOEt,6-Me | 163–165 | 2a/1d |
| 89 | Me | H | 2-MeO | 138–142 | 1c/2b |
| 90 | Me | Ph | 2-Cl,6-Me | 232–234 | 1c/2b |
| 91 | Me | Ph | 2,6-diF | 247–251 | 1c/1d |
| 92 | Me | Ph | 2,6-diCl,3-Me | 210–215 | 1c/1d |
| 93 | Me | Ph | 2-Cl,6-MeS | 248–250 | 1c/1d |
| 94 | Ph | Me | 2-COOMe,6-Me | 161–163 | 1c/1d |
| 95 | Me | H | 2-Cl,6-$NCCH_2$S | 197–200 | 1c/1d |
| 96 | $EtOOCCH_2$ | H | 2-COOEt,6-Me | oil | 1c/1d |
| 97 | H | H | 2,3-diCl,6-MeS | 256–258 | 3/2a/1d |
| 98 | Me | H | 2,3-diCl,6-MeS | 244–252 | 1c/1d |
| 99 | Me | H | 2-COOMe,6-MeO | 158–161 | 1c/1d |
| 100 | Me | Ph | 2-COOMe,6-Me | 157–158 | 1c/1d |
| 101 | Me | H | 2-$SO_2NH_2$ | 185–189 | 1c/1d |
| 102 | Me | H | 2-$OCHF_2$ | 184–186 | 1c/1d |
| 103 | Me | H | 2-$NO_2$ | 155–156 | 1c/1d |
| 104 | H | Me | 2-Cl,6-Me | 215–216 | 3/1c/2b |
| 105 | H | Me | 2,6-diF | 222–224 | 3/1c/2b |
| 106 | H | H | 2-COOallyl,6-Me | 102–104 | 1c/1d |
| 107 | Me | H | 2-OPh | 186–188 | 1c/1d |
| 108 | Me | H | 2-CN,3-F | 175–178 | 1c/1d |
| 109 | Me | H | 2-COObenzyl,6-Me | 131–133 | 1c/1d |
| 110 | Me | H | 2-COOallyl,6-Me | 113–115 | 1c/1d |
| 111 | H | H | 2-Cl,6-F | 223–225 | 1c/1d |
| 112 | Me | H | 2,6-diCOOMe | 157–159 | 1c/1d |

-continued

| No | R1 | R2 | R3 (Ph subst:) | M Pt (°C.) | Stages |
|---|---|---|---|---|---|
| 113 | Me | H | 2-Me,6-COOiPr | 111–112 | 1c/1d |
| 114 | H | H | 2-Me,6-COOiPr | 129–131 | |

The following compounds of formula I where $R^3$ represents 2-methoxycarbonyl-4-methylthien-3-yl were also prepared by methods analogous to those of Example 1:

| No | R1 | R2 | R4 | M Pt (°C.) | Stages |
|---|---|---|---|---|---|
| 115 | Me | Ph | H | 180–181 | 1c/1d |
| 116 | Me | H | H | 177–179 | 1c/1d |
| 117 | Me | Me | H | 167–168 | 1c/1d |

The following compound of formula I where $R^3$ represents 4-methylthiazol-2-yl was prepared by a method analogous to that of Example 1:

| No | R1 | R2 | R4 | M Pt (°C.) | Stages |
|---|---|---|---|---|---|
| 118 | Me | H | H | 203–206 | 1c/1d |

EXAMPLE 119

N,N-bis(6-methylthiazolo[3,2-b][1,2,4]triazole-2-sulphonyl)-2,6-dichloroaniline

The product of Example 1 stage (c) (3.0 g) was added portionwise with stirring and cooling to 2,6-dichloroaniline (2.1 g) in pyridine (10 ml). After stirring overnight, the mixture was treated with ether. The precipitated solid was filtered off and treated with ether and dilute hydrochloric acid. Filtration and drying gave 2.3 g of crude product, which was treated with warm acetone and filtered to give 1.1 g of pure product, mp 280°–290° C. with decomposition.

EXAMPLES 120–121

The following compounds of formula I corresponding to that of Example 119 but where $R^3$ is as indicated were prepared by methods analogous to that of Example 119:

| No | R3 | mp |
|---|---|---|
| 120 | 6-dichloro-3-methylphenyl | 280–286° C. |
| 121 | 2,6-dimethoxycarbonylphenyl | 283–285° C. |

EXAMPLE 122

N-(benzo[b]thiophen-4-yl)-6-methylthiazolo[3,2-b][1,2,4]triazole-2-sulphonamide

The product of Example 1 stage (c) (1.1 g) was added portionwise with stirring to 4-aminobenzo(b)thiophene (0.7 g) in dimethylaniline (4 ml.). The mixture was allowed to stand for 3 days prior to treatment with dilute hydrochloric acid and ether. The precipitated solid was isolated by filtration, washed with dilute hydrochloric acid, water and ether, and dried to give 1.4 g of crude product. This solid was treated with dilute ammonia solution, filtered, and the filtrate acidified. The precipitated product was filtered off, washed with water and ether, and dried to give 0.8 g of desired product, mp 205°–209° C.

EXAMPLE 123 (ALTERNATIVE INTERMEDIATE PREPARATION)

2-Benzylthiothiazolo[3,2-b][1,2,4]-triazole

The product of Example 3(a) (57.4 g) was refluxed in formic acid (350 ml) for 2 hours. The solution was then added to ice/water with stirring, and the product was extracted into ether. The ether solution was washed with water 3 times, dried and run down. The residue was recrystallised from ethanol to give 32.5 g of the desired product, mp 91°–93° C.

EXAMPLE 124 (ALTERNATIVE INTERMEDIATE PREPARATION)

2-Benzylthio-6-methoxy-5-methylthiazolo[3,2-b][1,2,4]triazole (a) 2-(3-Benzylthio-1,2,4-triazol-5-ylthio)propionic acid 3-Benzylthio-5-mercapto-1,2,4-triazole (56 g) was added with stirring and cooling to a solution of sodium hydroxide (10.1 g) in water (150 ml). A cold solution of 2-bromopropionic acid (38.4 g) in aqueous sodium hydroxide (10 g in 50 ml water) was added dropwise with stirring. The mixture was stirred for a further 6 hours at room temperature and allowed to stand overnight. After acidification with concentrated hydrochloric acid (30 ml), the precipitated white sticky solid was taken into ether. The ether solution was washed with water, dried, and the volume reduced to about 200 ml. The product crystallised, and was isolated by filtration to give 36.1 g of desired product, mp 123°–124° C. Successive reductions of the mother liquors gave further product, giving a total yield of 60 g.

(b) 2-Benzylthio-5-methylthiazolo[3,2-b][1,2,4]triazol-6(5H)-one

The product of stage (a) (57.9 g) was added portionwise to polyphosphoric acid (250 ml) at about 100° C. with stirring. Heating was continued for 30 minutes and the solution was then added to ice-water (1 l) and ethyl acetate (300 ml). The ethyl acetate solution was separated, and the aqueous phase was extracted with ethyl acetate. The organic phases were combined, washed with aqueous bicarbonate and water, dried and run down to give 49.3 g of crude product. Recrystallisation from ethanol gave 45.1 g of desired product, mp 85°–87° C.

(c) 2-Benzylthio-6-methoxy-5-methylthiazolo[3,2-b][1,2,4]triazole

Potassium t-butoxide (2.6 g) was added to a solution of the product of stage (b) in dimethylformamide (30 ml) with stirring and cooling. After 10 minutes, this solution was treated with dimethyl sulphate (2.8 g) and stirring was continued for 4 hours. Addition to ice-/water/ether and filtration gave 2.3 g of desired product, mp 101°–103° C.

INTERCONVERSION EXAMPLE A (A1) The product of Example 1 (1.4 g) was heated for 2 hours in acetic anhydride (5 ml) at reflux (145° C.). Cooling and addition to ether gave a crystalline product (1.2 g), which on recrystallisation from acetonitrile gave 0.7 g of the corresponding compound in which $R^4$ is acetyl, mp 192°–194° C.

(A2) The corresponding compound in which $R^4$ is isobutyryl was prepared from the product of Example 1 by an analogous method to that of (A1) above, mp 203°–205° C.:

(A3) Butanoyl chloride (1.0 g) was added dropwise to the product of Example 1 (3.0 g) in pyridine (10 ml) with stirring and ice cooling. The mixture was stirred for 3 hours and allowed to stand at room temperature overnight. Addition to water and ether, acidification and filtration yielded, after drying, 3.0 g of the corresponding compound in which $R^4$ is n-butanoyl, mp 177°–180° C.

(A4) The corresponding compound in which $R^4$ is methylsulphonyl was prepared from the product of Example 1 by an analogous method to that of (A3) above, mp 229°–232° C.

(A5) The corresponding compound in which $R^4$ is methoxycarbonyl was prepared from the compound of Example 1 by an analogous method to that of (A3) above, mp 207°–209° C.

INTERCONVERSION EXAMPLE B (B1)

6-Carboxymethyl-N-(2-chloro-6-methylphenyl)-thiazolo[3,2-b][1,2,4]-triazole-2-sulphonamide (Compound B1)

The product of Example 75 (2.0 g) was heated under reflux in concentrated hydrochloric acid (30 ml) with stirring for 26 hours. Dilution with water and filtration yielded, after drying, 1.7 g of the desired product, mp 268°–272° C.

The following compounds of the formula I were prepared by methods analogous to that of B1 above:

| No | R1 | R2 | R3 (Ph subst:) | R4 | M Pt (°C.) |
|---|---|---|---|---|---|
| B2 | Me | H | 2-COOH,6-Me | H | 279–280 |
| B3 | Me | COOH | 2,6-diF | H | 280–285 |

INTERCONVERSION EXAMPLE C

N-(2-carbamoyl-6-methylphenyl)-6-methylthiazolo[3,2-b][1,2,4]triazole-2-sulphonamide The product of Example B2 was heated under reflux for 2 hours in thionyl chloride (10 ml). The excess thionyl chloride was then removed under vacuum. The residue was treated with dichloromethane (30 ml) followed by 2 ml of 0.880 ammonia solution and 10 ml water, with stirring and ice-cooling. After 20 minutes, the mixture was filtered and the filtrate was acidified by the addition of concentrated hydrochloric acid (5 ml). The precipitated product was filtered off, washed with water and a little dichloromethane, and was dried, yielding 1.0 g of crude product. On recrystallisation from methanol/acetone, 0.65 g of the desired pure amide, mp 217°–218° C., were obtained.

INTERCONVERSION EXAMPLE D

N-(2-chloro-6-methylsulphinylphenyl)-6-methylthiazolo[3,2-b][1,2,4]-triazole--2-sulphonamide Hydrogen peroxide (30%, 0.8 g) was added to a suspension of the product of Example 40 (2.5 g) in acetic acid (20 ml) with stirring. The mixture was stirred intermittently at room temperature for 45 days. The product was then filtered off and recrystallised from dimethylformamide, yielding 1.0 g of the desired sulphoxide, mp 271°–273° C.

INTERCONVERSION EXAMPLE E

N-(2-chloro-6-methylphenyl)-N,6-dimethyl-thiazolo[3,2-b][1,2,4]triazole-2-sulphonamide To a solution of the product of Example 1 (3 g) in dimethylformamide (20 ml) was added potassium t-butoxide (1.1 g) with cooling and stirring. Dimethyl sulphate (0.92 ml) was added dropwise, and the reaction mixture was stirred overnight. Addition to ice-/water/ether and filtration, followed by recrystallisation from ethyl acetate gave 1.9 g of the desired product, mp 178°–180° C.

EXAMPLES E2–E3

The following compounds corresponding to that of Example E, but where $R^4$ is as indicated were prepared by methods analogous to that of Example E:

| No | R4 | mp (°C.) |
|---|---|---|
| E2 | allyl | 103–105 |
| E3 | benzyl | 140–141 |

FORMULATION EXAMPLES

A 10% suspension concentrate formulation of the compound of Example 71 was prepared from the following:

|  | g/l |
|---|---|
| Compound 71 | 100 |
| Pluronic P75 | 30 |
| Polyfon H | 20 |
| Propylene glycol | 105 |
| Anti-foam 1520 | 0.5 |
| Veegum R | 7.5 |
| Kelzan (xanthan gum) | 1.0 |
| Formaldehyde (40% aq solution) | 1.0 |
| Water | to 1 liter |

Analogous formulations were prepared containing 0.5, 5, 10, 25, 50 and 85% by weight of the compounds of Examples 1–124, A1–A5, B1–B3, C, D and E1–E3.

HERBICIDAL EXAMPLE A (Pre-Emergence)

Seeds of the weed species listed below were sown in anodised aluminium pans 19 cm long×9.5 cm wide×6 cm deep, containing sterilized sandy loam. They were watered and then sprayed with the compounds of the Examples listed below formulated as a solution/suspension in 1:1 by volume of acetone and the wetting agent polyoxyethylene (20 mols) monolaurate solution (2 g per liter).

The concentration of each test compound and volume of application were calculated to give the desired rate of application of the compound in 450 liters per hectare. After 3 to 4 weeks growth in the controlled environment room (20° C.; 75–95% relative humidity; 14 hours per day artificial illumination) the plants were visually assessed for any herbicidal response.

All differences from an untreated control were scored accordingly to an index where 0=no effect, 1=1–24% effect, 2=25–69% effect, 3=70–89% effect and 4=90–100% effect. In the table below, the following letters are used to denote the plant species:

a—*Polygonum lapathifolium* (Pale persicaria)
b—*Galium aparine* (cleavers)
c—*Chrysanthemum segetum* (corn marigold)
d—*Alopecurus myosuroides* (blackgrass)
e—*Elymus repens* (Couchgrass)
f—*Avena fatua* (wild oat)
g—*Abutilon theophrasti* (velvetleaf)
h—*Cyperus rotundus* (purple nutsedge)
i—*Pharbitis purpurea* (morningglory)
j—*Echinochloa crus-galli* (barnyardgrass)
k—*Setaria viridis* (green foxtail)
l—*Solanum nigrum* (black nightshade)

The results obtained were as follows:

| Ex | Kg/ha | a | b | c | d | e | f | g | h | i | j | k | l |
|---|---|---|---|---|---|---|---|---|---|---|---|---|---|
| 1 | 2.5 | 4 | 4 | 4 | 2 | 2 | 2 | 4 | 3 | 3 | 3 | 3 | 4 |
| 3 | 2.5 |   | 4 | 4 | 3 | 4 | 2 | 4 | 3 | 3 | 4 | 4 | 4 |
| 4 | 2.5 | 4 | 4 | 4 | 2 | 2 | 0 | 4 | 4 | 3 | 3 | 2 | 4 |
| 5 | 2.5 |   | 4 | 4 | 2 | 2 | 1 | 4 | 2 | 3 | 2 | 2 | 3 |
| 6 | 2.5 |   | 2 | 4 | 2 | 0 | 0 | 4 | 3 | 3 | 0 | 0 | 4 |
| 7 | 2.5 |   | 2 | 3 | 2 | 2 | 2 | 2 | 2 | 2 | 2 | 3 | 4 |
| 8 | 2.5 | 4 | 4 | 4 | 3 | 4 | 0 | 4 | 4 | 4 | 3 | 3 |   |
| 9 | 1 | 0 | 0 | 4 | 2 | 0 | 0 | 3 | 2 | 0 | 0 | 0 |   |
| 15 | 1 | 4 | 4 | 4 | 0 | 0 | 0 | 4 | 3 | 0 | 2 | 2 | 4 |
| 17 | 1 | 2 | 2 | 4 |   | 0 | 1 | 0 | 0 | 0 | 0 | 0 | 3 |
| 19 | 1 | 1 | 4 | 4 | 2 | 0 | 0 | 2 | 0 | 0 | 0 | 2 | 2 |
| 21 | 1 | 2 | 0 | 3 | 0 | 0 | 0 | 2 | 0 | 1 | 0 | 0 | 4 |
| 23 | 1 | 4 | 4 | 0 | 0 | 0 | 0 | 1 | 0 | 1 | 0 | 2 | 4 |
| 24 | 1 | 3 | 4 | 4 | 3 | 4 | 0 | 3 | 0 | 2 | 2 | 2 | 4 |
| 26 | 1 | 2 | 2 | 4 | 4 | 0 | 1 | 3 | 0 | 0 | 0 | 0 |   |
| 32 | 1 | 2 | 2 | 4 | 2 | 0 | 0 | 2 | 0 | 0 | 2 | 2 |   |
| 33 | 1 | 2 | 4 | 4 | 0 | 0 | 0 | 2 | 0 | 1 | 0 | 0 |   |
| 35 | 1 | 4 | 3 | 4 | 2 | 0 | 0 | 4 | 4 | 3 | 4 | 2 | 4 |
| 36 | 1 | 3 | 4 | 4 | 0 | 2 | 0 | 3 | 0 | 1 | 0 | 0 | 2 |
| 40 | 1 | 3 | 4 | 4 | 0 | 0 | 0 | 2 | 2 | 0 | 0 | 0 | 4 |
| 43 | 1 | 0 | 0 | 4 | 0 | 0 | 0 | 2 | 0 | 1 | 0 | 0 |   |
| 58 | 1 | 4 | 4 | 4 | 3 | 2 | 2 | 4 | 4 | 4 | 4 | 4 |   |
| 59 | 1 | 2 | 0 | 0 | 0 | 0 | 0 | 0 | 0 | 0 | 0 | 0 | 4 |
| 62 | 0.5 | 4 | 4 | 4 | 2 | 2 | 2 | 4 | 3 | 2 | 4 | 4 | 4 |
| 65 | 0.5 | 2 | 0 | 2 | 0 | 0 | 0 | 0 | 0 | 0 | 0 | 2 | 4 |
| 73 | 1 | 4 | 4 | 4 | 4 | 4 | 4 | 4 | 4 | 4 | 4 | 4 | 4 |
| 76 | 0.5 | 3 |   | 3 | 0 | 2 | 0 | 3 | 0 | 3 | 4 | 2 | 4 |
| 77 | 0.5 | 2 | 3 | 3 | 0 | 0 | 2 | 3 | 0 | 2 | 2 | 0 | 4 |
| 82 | 1 | 0 | 0 | 2 | 0 | 0 | 4 | 2 | 0 | 0 | 0 | 0 |   |
| 83 | 1 | 0 |   | 4 | 0 | 0 | 0 | 0 | 0 | 2 | 0 | 0 |   |
| 85 | 1 | 0 | 0 | 4 | 0 | 0 | 0 | 3 | 0 | 0 | 0 | 0 |   |
| 86 | 1 | 2 | 4 | 4 | 0 | 2 | 0 | 4 | 3 | 1 | 2 | 2 | 4 |
| 87 | 1 | 2 | 4 | 4 | 0 | 0 | 0 | 1 | 0 | 3 | 2 | 0 | 4 |
| 88 | 1 | 3 | 0 | 0 | 0 | 0 | 0 | 2 | 2 | 0 | 0 | 0 | 4 |
| 103 | 2.5 | 4 | 3 | 3 | 2 | 0 | 0 | 3 | 2 | 2 | 0 | 2 | 2 |
| 104 | 1 | 4 | 4 | 2 | 2 | 0 | 0 | 4 | 0 | 2 | 4 | 2 | 4 |
| 105 | 1 | 4 | 4 | 4 | 3 | 4 | 2 | 4 | 0 | 3 | 4 | 2 | 4 |
| 119 | 2.5 | 3 | 3 | 4 | 2 | 2 | 0 | 2 | 2 | 1 | 0 | 0 | 4 |
| 122 | 2.5 | 4 | 3 | 3 | 2 | 0 | 0 | 4 | 3 | 0 | 2 | 3 | — |
| A1 | 2.5 | 4 | 4 | 4 | 2 | 2 | 0 | 3 | 2 | 2 | 3 | 3 | 4 |

HERBICIDAL EXAMPLE B
(POST-EMERGENCE)

Seeds of the plant species listed below were sown in anodised aluminium pans, 19 cm long×9.5 cm×6 cm deep, containing sterilised sandy loam. They were then watered and placed in a controlled environment room (20° C.; 75-95% relative humidity; 14 hours per day artificial illumination). Fourteen or twenty one days after sowing (depending on the species but when most plants had 2 to 3 true leaves) the seedlings received a foliar spray of the compounds of the Examples listed below, formulated as a solution/suspension in 1:1 by volume of acetone and the wetting agent polyoxyethylene (20 mols) monolaurate solution (2 g per liter).

The concentration of each test compound was calculated to give the desired rate of application of the compound in 450 liters per hectare. After 2 to 3 weeks growth in the controlled environment room the plants were visually assessed for any herbicidal response.

All differences from an untreated control were scored according to an index where 0=no effect, 1=1-24% effect, 2=25-69% effect, 3=70-89% effect and 4=90-100% effect. In the table below, the following letters are used to denote the plant species:

a—*Polygonum lapathifolium* (Pale persicaria)
b—*Galium aparine* (cleavers)
c—*Chrysanthemum segetum* (corn marigold)
d—*Alopecurus myosuroides* (blackgrass)
e—*Elymus repens* (Couchgrass)
f—*Avena fatua* (wild oat)
g—*Abutilon theophrasti* (velvetleaf)
h—*Cyperus rotundus* (purple nutsedge)
i—*Pharbitis purpurea* (morningglory)
j—*Echinochloa crus-galli* (barnyardgrass)
k—*Setaria viridis* (green foxtail)
l—*Solanum nigrum* (black nightshade)

The results obtained were as follows:

| Ex | Kg/ha | a | b | c | d | e | f | g | h | i | j | k | l |
|---|---|---|---|---|---|---|---|---|---|---|---|---|---|
| 1 | 2.5 | 4 | 3 | 2 | 3 | 2 | 2 | 4 | 2 | 2 | 3 | 3 | 4 |
| 4 | 2.5 | 3 | 3 | 3 | 0 | 0 | 1 | 4 | 2 | 2 | 2 | 2 | 4 |
| 5 | 2.5 | 2 | 2 | 3 | 2 | 0 | 1 | 4 | 1 | 1 | 1 | 1 | 2 |
| 3 | 2.5 | 3 | 3 | 1 | 2 | 2 | 3 | 3 | 1 | 1 | 3 | 3 | 2 |
| 15 | 1 | 3 | 3 | 3 | 1 | 0 | 0 | 2 | 0 | 1 | 2 | 1 | 3 |
| 24 | 1 | 2 | 3 | 2 | 0 | 0 | 1 | 4 | 0 | 2 | 1 | 1 | 4 |
| 35 | 1 | 2 | 3 | 4 | 2 | 0 | 0 | 4 | 1 | 2 | 3 | 2 | 4 |
| 36 | 1 | 0 | 3 | 4 | 0 | 0 | 1 | 4 | 1 | 2 | 2 | 2 | 3 |
| 40 | 1 | 1 | 3 | 4 | 1 | 0 | 0 | 4 | 1 | 1 | 2 | 2 | 3 |
| 62 | 0.5 | 3 | 3 | 2 | 1 | 0 | 0 | 4 | 2 | 2 | 2 | 2 | 3 |
| 105 | 1 |   | 4 | 4 | 3 | 2 | 0 | 4 | 1 | 2 | 1 | 2 | 2 |
| 122 | 2.5 | 1 | 3 | 1 | 2 | 0 | 1 | 1 | 1 | 1 | 3 | 3 | 4 |
| A1 | 2.5 | 3 | 2 | 1 | 2 | 3 | 2 | 3 | 0 | 1 | 3 | 3 | 3 |

I claim:
1. A thiazolotriazole sulphonamide of the formula:

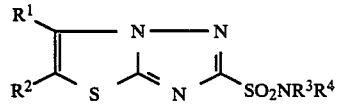

where:
R[1] and R[2], which may be the same or different, each represent hydrogen; hydroxy; halo; cyano; halo, carboxy, cyano or alkoxycarbonyl of 1 to 4 carbon atoms substituted or unsubstituted alkyl or alkoxy of 1 to 6 carbon atoms; alkenyloxy or alkynyloxy of 2 to 6 carbon atoms, fluoro or chloro and methyl substituted or unsubstituted phenyl or benzyl; a 5- or 6-membered single ring nitrogen containing heteraryl group, or carbamoyl; or a group —COR$^a$ or —CO$_2$R$^a$ where R$^a$ is hydrogen or alkyl of 1 to 6 carbon atoms; or R[1] and R[2] together represent an alkylene chain of 3 or 4 carbon atoms;

R[3] represents unsubstituted phenyl or phenyl substituted by one or more alkyl, alkoxy, alkoxycarbonyl or alkylthio groups of 1 to 4 carbon atoms (which may themselves be further substituted by cyano or halogen), cyano groups, aminosulphonyl groups, halogen atoms or nitro groups, a 5- or 6-membered heterocyclic group which contains nitrogen, oxygen or sulfur or benzheterocyclyl group; and $R^4$ represents hydrogen, an alkali-metal atom, an ammonium group, a halo, carboxy, cyano or alkoxycarbonyl of 1 to 4 carbon atoms, alkenyl or alkynyl of 2-6 carbon atoms, acyl, alkoxycarbonyl of 2 to 6 carbon atoms, benzyl or a 5- or 6-membered single ring nitrogen containing heterocyclic group, or a group of the formula:

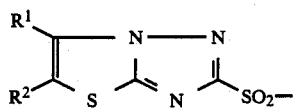

where $R^1$ and $R^2$ are as defined hereinbefore.

2. Thiazolotriazole sulphonamide according to claim 1 wherein $R^1$ represents hydrogen or an unsubstituted alkyl group of 1 to 6 carbon atoms.

3. Thiazolotriazole sulphonamide according to claim 1 wherein $R^2$ represents hydrogen or an unsubstituted alkyl group of 1 to 6 carbon atoms.

4. Thiazolotriazole sulphonamide according to claim 1 wherein $R^3$ represents a phenyl group, which is substituted by one or more alkyl, alkoxy, alkoxycarbonyl or alkylthio groups of 1 to 4 carbon atoms (which may themselves be further substituted), cyano groups, aminosulphonyl groups, or nitro groups.

5. Thiazolotriazole sulphonamide according to claim 1 wherein $R^4$ represents hydrogen.

6. Thiazolotriazole sulphonamide according to claim 1 wherein $R^1$ and $R^2$ each represent hydrogen or methyl, $R^3$ is a phenyl group substituted by one or more alkyl, alkoxy, alkoxycarbonyl or alkylthio groups of 1 to 4 carbon atoms, halogen atoms or nitro groups, and $R^4$ is hydrogen.

7. N-(2,6-difluorophenyl)thiazolo[3,2-b][1,2,4]triazole-2-sulphonamide.

8. A herbicidal composition which comprises one or more compounds according to claim 1 in association with a suitable carrier and/or surface active agent.

9. Thiazolotriazole sulphonamide according to claim 2 where $R^2$ represents hydrogen or an unsubstituted alkyl group of 1 to 6 carbon atoms.

10. Thiazolotriazole sulphonamide according to claim 9 wherein $R^3$ represents a phenyl group, which is substituted by one or more alkyl, alkoxy, alkoxycarbonyl or alkylthio groups of 1 to 4 carbon atoms (which may themselves be further substituted), halogen atoms, cyano groups, aminosulphonyl groups, or nitro groups.

11. Thiazolotriazole sulphonamide according to claim 10 wherein $R^4$ represents hydrogen.

12. A herbicidal composition according to claim 8 wherein in said thiazolotriazole sulphonamide, $R^1$ represents hydrogen or an unsubstituted alkyl group of 1 to 6 carbon atoms.

13. Thiazolotriazole sulphonamide according to claim 12 wherein $R^2$ represents hydrogen or an unsubstituted alkyl group to 1 to 6 carbon atoms.

14. Thiazolotriazole sulphonamide according to claim 13 wherein $R^3$ represents a phenyl group, which is substituted by one or more alkyl, alkoxy, alkoxycarbonyl or alkylthio groups of 1 to 4 carbon atoms (which may themselves be further substituted), halogen atoms, cyano groups, aminosulphonyl groups, or nitro groups.

15. Thiazolotriazole sulphonamide according to claim 14 wherein $R^4$ represents hydrogen.

16. A herbicidal composition according to claim 8 in which said compound is N-(2,6-difluorophenyl)-thiazolo[3,2-b][1,2,4]triazole-2-sulphonamide.

17. In the method applying a herbicidally active compound to an area in which herbicidal activity is desired, the improvement which comprises employing the thiazolotriazole sulphonamide of claim 1 as said herbicidally active compound.

18. In the method applying a herbicidally active compound to an area in which herbicidal activity is desired, the improvement which comprises employing the thiazolotriazole sulphonamide of claim 6 as said herbicidally active compound.

19. In the method applying a herbicidally active compound to an area in which herbicidal activity is desired, the improvement which comprises employing the thiazolotriazole sulphonamide of claim 7 as said herbicidally active compound.

* * * * *